United States Patent [19]

Cassidy et al.

[11] 4,264,736

[45] Apr. 28, 1981

[54] ANTIBIOTIC 890A$_{10}$

[75] Inventors: Patrick J. Cassidy, Rahway; Sheldon B. Zimmerman, Springfield; Josefino B. Tunac, Somerset, all of N.J.; Sebastian Hernandez, Madrid, Spain

[73] Assignee: Merck & Co., Inc., Rahway, N.J.

[21] Appl. No.: 79,122

[22] Filed: Sep. 26, 1979

Related U.S. Application Data

[63] Continuation of Ser. No. 891,799, Mar. 30, 1978, abandoned, which is a continuation of Ser. No. 742,958, Nov. 17, 1976, abandoned.

[51] Int. Cl.$^3$ .............................................. C12P 17/18
[52] U.S. Cl. ..................................... 435/119; 435/886
[58] Field of Search .............................. 435/119, 886

[56] References Cited

U.S. PATENT DOCUMENTS 4,162,304  7/1979  Box et al. .............................. 424/117

FOREIGN PATENT DOCUMENTS 839324  9/1976  Belgium .............................. 260/326.31

OTHER PUBLICATIONS

Derwent Abstract, 72175x, Beecham Group Ltd., 9/8/76.
Beecham Group Ltd., British Patent Application No. 10914/1975.

Primary Examiner—Robert J. Warden
Attorney, Agent, or Firm—Frank M. Mahon; Julian S. Levitt

[57] ABSTRACT

The antibiotic MSD 890A$_{10}$ and pharmaceutically acceptable salts thereof (hereinafter referred to as antibiotic 890A$_{10}$) is active against both gram-positive and gram-negative bacteria. The antibiotic is produced by growing species of Streptomyces on suitable fermentation media.

2 Claims, No Drawings

ANTIBIOTIC 890A$_{10}$

This is a continuation of application Ser. No. 891,799 filed Mar. 30, 1978, now abandoned which in turn is a continuation of U.S. Ser. No. 742,958 filed Nov. 17, 1976, now abandoned.

BACKGROUND OF THE INVENTION

The discovery of the remarkable antibiotic properties of penicillin stimulated great interest in this field which has resulted in the finding of many other valuable antibiotic substances. In general, the antibacterial activity of each of these antibiotics does not include certain clinically important pathogenic bacteria. For example, some are principally active against only gram-positive types of bacteria. Acquired resistance over the course of widespread use of existing antibiotics in the treatment of bacterial infection has caused a serious resistance problem to arise.

Accordingly, the deficiencies of the known antibiotics have stimulated further research to find other antibiotics which will be active against a wider range of pathogens as well as resistant strains of particular microorganisms.

SUMMARY OF THE INVENTION

This invention is directed to a new antibiotic agent. It is concerned with a new antibiotic substance, herein designated 890A$_{10}$. The invention encompasses the antibiotic in dilute form, as crude concentrate and in pure form.

It is an object of the present invention to provide a new and useful antibiotic which is highly effective in inhibiting the growth of various gram-negative and gram-positive microorganisms. Another object is to provide a process for the preparation of the novel antibiotic substance by the fermentation of nutrient media with species of Streptomyces. Other objects will be apparent from the detailed description of this invention hereinafter provided.

The novel antibiotic substance of the present invention is produced by growing under controlled conditions a new strain of *Streptomyces flavogriseus.*

Based upon extensive taxonomic studies, the strain of microorganism used in the present invention was identified as belonging to the species *Streptomyces flavogriseus* and has been designated MA-4638 in the culture collection of MERCK & CO., Inc., Rahway, N.J. A culture thereof has been placed on permanent deposit without restrictions as to availability with the culture collection of the Northern Regional Laboratories, Northern Utilization Research and Development Division, Agricultural Research Service, U.S. Department of Agriculture, Peoria, Ill., and is available to the public under accession No. NRRL 11,020.

*Streptomyces flavogriseus* MA-4638 produces antibiotic 890A$_{10}$ which is isolated in substantially pure form from the fermentation broth.

The morphological and cultural characteristics of *Streptomyces flavogriseus* MA-4638 are set forth in the following table.

Morphology

Sporophores are branching, straight to flexuous chains of spores, forming tufts. Chains are more than 10 spores in length. Spores are spherical to oval - 0.9$\mu \times$ 1.2$\mu$(970$\times$).

Cultural Characteristics

Oatmeal agar (ISP Medium 3)
  Vegetative growth—Reverse-yellow-tan edged with brown, wrinkled;
  Aerial mycelium—Light gray edged with medium gray
  Soluble pigment—None.
Czapek Dox agar (sucrose nitrate agar)
  Vegetative growth—Reverse-brown edged with dark brown;
  Aerial mycelium—Medium gray, velvety;
  Soluble pigment—Slight browning of medium.
Egg albumin agar
  Vegetative growth—Reverse-yellow-tan edged with brown;
  Aerial mycelium—Medium gray mixed with yellowish gray (2dc) and grayed yellow (2db);
  Soluble pigment—Light yellowish tan.
Glycerol asparagine agar
  Vegetative growth—Reverse-brown;
  Aerial mycelium—Velvety, light gray with yellowish tone (2dc);
  Soluble pigment—Light tan.
Inorganic salts-starch agar (ISP Medium 4)
  Vegetative growth—Reverse-greenish-yellowish-tan;
  Aerial mycelium—velvety, medium gray with yellow tone (3fe);
  Soluble pigment—Very light tan.
Yeast extract-dextrose+salts agar
  Vegetative growth—Reverse-dark brown;
  Aerial mycelium—Dark gray mixed with a lighter gray;
  Soluble pigment—None.
Yeast extract-malt extract agar (ISP Medium 2)
  Vegetative growth—Reverse-brown;
  Aerial mycelium—Velvety, dark gray edged with a lighter gray;
  Soluble pigment—None.
Skim milk agar
  Vegetative growth—Tan;
  Aerial mycelium—Sparse, whitish;
  Soluble pigment—Slight browning of medium;
  Hydrolysis of casein—Good.
Litmus milk
  Vegetative growth—Moderate growth ring, tan;
  Aerial mycelium—None;
  Color—Purple;
  Coagulation and/or peptonization—Complete peptonization; becoming alkaline.
Skim milk
  Vegetative growth—Moderate growth ring, tan;
  Aerial mycelium—None;
  Soluble pigment—Light brown;
  Coagulation and/or peptonization—Complete peptonization; becoming alkaline.
Nutrient tyrosine agar
  Vegetative growth—Reverse-dark brown;
  Aerial mycelium—Dark gray edged with grayish white;
  Soluble pigment—Slight browning of medium;
  Decomposition of tyrosine—Positive.
Peptone-iron-yeast extract agar
  Vegetative growth—Tan;
  Aerial mycelium—whitish, moderate;
  Soluble pigment—None;
  Melanin—None;

H₂S production—Negative.
Nutrient agar
  Vegetative growth—Reverse-light grayish brown;
  Aerial mycelium—Light gray edged with dark gray;
  Soluble pigment—None.
Nutrient starch agar
  Vegetative growth—Tan edged with gray;
  Aerial mycelium—Medium gray;
  Soluble pigment—None;
  Hydrolysis of starch—Good.
Nutrient gelatin agar
  Vegetative growth—Tan edged with gray;
  Aerial mycelium—Grayish-white;
  Soluble pigment—None;
  Liquefaction of gelatin—Good.
Potato plug
  Vegetative growth—Tan;
  Aerial mycelium—Medium to dark gray;
  Soluble pigment—None.
Loeffler's Blood serum
  Vegetative growth—Cream-colored;
  Aerial mycelium—None;
  Soluble pigment—None;
  Liquefaction—None.
Gelatin stabs
  Vegetative growth—Tan;
  Aerial mycelium—None;
  Soluble pigment—None;
  Liquefaction of gelatin—Complete.

All of the readings reported above were taken after three weeks incubation at 28° C. unless noted otherwise. The pH of the media used in these studies was approximately neutral, namely, pH 6.8–7.2. The color designations used in the description are in accordance with the definitions of the Color Harmony Manual, 4th Edition (1958), Container Corporation of America, Chicago, Illinois. Streptomyces flavogriseus MA-4638 was also tested for its ability to utilize or assimilate various carbohydrates. For this purpose, the microorganism was grown on basal synthetic medium (Pridham and Gottlieb) containing 1% of the carbohydrate at 28° C. for three weeks. The pH of the media employed in the study was approximately neutral (6.8–7.2). Table I shows the utilization of these carbohydrate sources by Streptomyces flavogriseus MA-4638; + indicating growth, ± poor or questionable growth, and − no growth as compared to negative control (no carbon source).

TABLE I

| Glucose | + | Maltose | + |
|---|---|---|---|
| Arabinose | + | Mannitol | + |
| Cellulose | − | Mannose | + |
| Fructose | + | Raffinose | − |
| Inositol | − | Rhamnose | + |
| Lactose | + | Sucrose | ± |
| Xylose | + | | |

The amount of growth with change in temperature and the oxygen requirement by the microorganism is as follows:
Temperature range (Yeast extract-dextrose+salts agar);
  28° C.—Good vegetative and aerial growth
  37° C.—Good vegetative growth; no aerial hyphae
  50° C.—No growth
Oxygen requirement (Stab culture in yeast extract-dextrose+salts agar);
  Aerobic The present invention is not limited to the organism, Streptomyces flavogriseus or to organisms fully answering the above growth and microscopic characteristics which are given for illustrative purposes. It is desired and intended to include the use of mutants produced from the described organism by various means, such as X-radiation, ultraviolet radiation, nitrogen mustard, phage exposure and the like.

890A$_{10}$ is produced during the aerobic fermentation, under controlled conditions, of suitable aqueous nutrient media inoculated with a strain of the organism, Streptomyces flavogriseus. Aqueous media, such as those employed for the production of other antibiotics, are suitable for producing 890A$_{10}$. Such media contain sources of carbon, nitrogen and inorganic salts assimilable by the microorganism.

In general, carbohydrates such as sugars, for example, dextrose, glucose, fructose, maltose, sucrose, xylose, mannitol and the like and starches such as dextrin or such as grains, for example, oats, rye, cornstarch, corn meal and the like can be used either alone or in combination as sources of assimilable carbon in the nutrient medium. The amount of carbohydrate usually varies between about 1% and 6% by weight of the medium. These carbon sources can be used individually, or several such carbon sources may be combined in the medium. In general, many proteinaceous materials may be used as nitrogen sources in the fermentation process. Suitable nitrogen sources include, for example, yeast hydrolysates, primary yeast, soybean meal, cottonseed flour, hydrolysates of casein, corn steep liquor, distiller's solubles or the like, the preferred source being distiller's solubles. The sources of nitrogen, either alone or in combination, are used in amounts ranging from about 0.2% to 6% by weight of the aqueous medium.

Among the nutrient inorganic salts which can be incorporated in the culture media are the customary salts capable of yielding sodium, potassium, ammonium, calcium, magnesium, phosphate, sulfate, chloride, carbonate, and like ions. Also included are trace metals such as cobalt, manganese and iron.

The media described in the Examples are merely illustrative of the wide variety of media which may be employed, and are not intended to be limitative.

The fermentation is carried out at temperatures ranging from about 20° to 37° C.; however, for optimum results it is preferable to conduct the fermentation at temperatures of from about 23° to 28° C. The initial pH of the nutrient media suitable for growing strains of the Streptomyces flavogriseus culture and producing antibiotic 890A$_{10}$ can vary from about 6.0 to 8.0.

Although the novel antibiotic 890A$_{10}$ is produced by both surface and submerged cultures, it is preferred to carry out the fermentation in the submerged state.

A small scale fermentation of the antibiotic is conveniently carried out by inoculating a suitable nutrient medium with the antibiotic-producing culture and, after transfer to a production medium, permitting the fermentation to proceed at a constant temperature of about 24° C. on a shaker for several days.

The fermentation is initiated in a sterilized flask of nutrient medium via one or more stages of seed development. The nutrient medium for the seed stage may be any suitable combination of carbon and nitrogen sources. The seed flask is shaken in a constant temperature chamber at about 28° C. for one day, or until growth is satisfactory, and some of the resulting growth is used to inoculate either a second stage seed or the production medium. Intermediate stage seed flasks, when used, are developed in essentially the same manner; that is, part of the contents of the flask from the last seed stage are used to inoculate the production medium. The inoculated flasks are shaken at a constant temperature for several days, and at the end of the incubation period the contents of the flask are centrifuged or filtered.

For large scale work, it is preferable to conduct the fermentation in suitable tanks provided with an agitator and a means of aerating the fermentation medium. According to this method, the nutrient medium is made up in the tank and sterilized by heating at temperatures of up to about 120° C. Upon cooling, the sterilized medium is inoculated with a previously grown seed of the producing culture, and the fermentation is permitted to proceed for a period of time as, for example, from 1 to 6 days while agitating and/or aerating the nutrient medium and maintaining the temperature at about 22° to 26° C. This method of producing antibiotic $890A_{10}$ is particularly suited for the preparation of large quantities of the antibiotic.

Physical and Chemical Properties of Antibiotic $890A_{10}$

Antibiotic $890A_{10}$ is an acidic substance which migrates toward the positive pole on electrophoresis at neutral pH. At a gradient of 50 volts/cm. in 0.03 M potassium phosphate buffer, pH 7.1, the antibiotic moves 8.0 cm. in 30 minutes, compared with a movement of 4.0 cm. for $890A_1$. The disodium salt is a white or slightly yellow powder as lyophilized from aqueous solution. Under acidic conditions in aqueous solution, the antibiotic is unstable, and the free acid form has not been isolated.

The disodium salt of antibiotic $890A_{10}$ has an absorption maximum at 299 nm and a minimum at 243 nm at neutral pH in water. The E% at 300 nm of the most highly purified preparation of disodium salt is 214. The ratio $A_{300}/A_{250}$ is 3.33 for the most purified sample, and the ratio $A_{300}/A_{220}$ is 2.05. Evidence of slight impurities in this sample suggests that the corresponding ratios for a sample of ultimate purity would be somewhat higher. More than 94% of the absorption at 300 nm can be extinguished by reaction with hydroxylamine at neutral pH. The absorbance at 250 nm also decreases upon reaction with hydroxylamine, and the ratio of the absorbance decrease at 250 nm to the decrease at 300 nm, is approximately 0.16. The reaction with hydroxylamine, as followed by $A_{300}$ decrease under the conditions described in the section "Hydroxylamine Reaction" is apparently first order, with a half-life at room temperature of from 23 to 60 seconds.

When measured against a standard of antibiotic $890A_1$, the antibiotic $890A_{10}$ has 174 bioassay units per $HAEA_{300}$ unit. $HAEA_{300}$ is described at page 25 under the section "Hydroxylamine Reaction".

Table II lists the 100 MHz-nuclear magnetic resonance spectral signal of $890A_{10}$ in $D_2O$ at 32° C. Chemical shifts are given in ppm relative to HOD at $4.70\delta$ at 32° C., and coupling constants in Hertz.

TABLE II

| | |
|---|---|
| $CH_3CH$ | 1.55 (3H;d;6.5 Hz) |
| $CH_3CO$ | 2.02 (3H; s; |
| $C_{(6)}$—M | 3.89 (1H;d,d;$J_{6-5}$ = 5.4 Hz;$J_{6-8}$ = 9.2 Hz) |
| $C_{(5)}$—H | ~4.34 (1H;d,t;$J_{5-6}$ = 5.5 Hz;$J_{5-1}$ = 9.5 Hz) |
| $C_{(8)}$—H | ~4.8 (partially covered by HOD line) |
| $C_{(1)}$—$H_2$ | ~3.14 (1H;d,d;~9.2 + ~18 Hz) |
| | ~3.33 (1H;d,d;~10 + 18 Hz) |

TABLE II-continued

| | |
|---|---|
| —$CH_2NH$ | 3.43 (2H;t;7Hz) |
| —$CH_2$—S— | 3.03 (2H,m) |

The mass spectra of TMSi-$890A_{10}$ is characterized by fragments as shown in Table III.

TABLE III

| m/e | |
|---|---|
| | 86 |
| | 227.0224 $C_5H_{15}SO_4Si_2$, calc. 227.0230 |
| | 241 |
| | 300/1 |
| | 339.1325 $C_{15}H_{25}NO_4Si_2$, calc. 339.1322 |
| | 342.1444 $C_{15}H_{26}N_2O_3S$ Si, calc. 342.1433 |
| | 363 |
| | 440 |
| | 458 |

Antibiotic $890A_{10}$ has a molecular structure as follows:

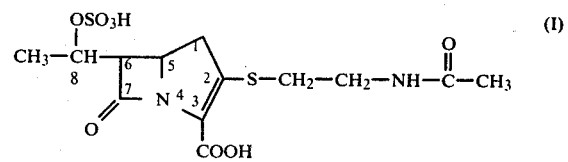

(I)

Antibiotic $890A_{10}$ is further characterized by the following antibiotic spectrum profiles.

The test to determine the antibiotic spectrum profiles of antibiotic $890A_{10}$ is carried out by application of a 0.015 ml. droplet of a 9.5 μg./ml. aqueous solution of the antibiotic on the surface of a 100×15 mm. petri plate containing 3 ml. of seeded nutrient agar plus 0.2% yeast extract which is incubated at 25° C. The results, expressed in terms of the diameter in millimeters of the zone of inhibition, are set forth in Table IV.

TABLE IV

| Organism | Inhib. Zone Diam., mm |
|---|---|
| Bacillus sp. MB No. 633 | 30 |
| Proteus vulgaris MB No. 1012 | 19 |
| Pseudomonas aeruginosa MB No. 979 | 0 |
| Serratia marcescens ATCC 890 | 15 |
| Staphylococcus aureus ATCC 6538 P | 20 |
| Bacillus subtilis ATCC 6633 | 30 |
| Sarcina lutea ATCC 9341 | 33 |
| Staphylococcus aureus MB No. 698 | 23 |
| Streptococcus faecalis MB No. 753 | 0 |
| Alcaligenes faecalis ATCC 213 | 24 |
| Brucella bronchiseptica ATCC 4617 | 0 |
| Salmonella gallinarum MB No. 1287 | 28 |
| Vibrio percolans ATCC 8461 | 33 |
| Xanthomonas vesicatoria MB No. 815 | 20 |
| Proteus vulgaris ATCC 21100 | 30 |
| Escherichia coli MB No. 1418 | 25 |
| Pseudomonas stutzeri ATCC 11607 | 0 |
| Klebsiella pneumoniae MB No. 1264 | 19 |
| Aerobacter aerogenes MB No. 835 | 22 |
| Erwinia atroseptica ATCC 4446 | 10 |
| Pseudomonas aeruginosa MB No. 2824 | 0 |
| Corynebacterium psedodiph. ATCC 9742 | 12 |
| Escherichia coli ATCC 9637 | 17 |
| Streptococcus faecium MB No. 2820 | 0 |
| Streptococcus agalactiae MB No. 2875 | 29 |
| Vibrio percolans MB No. 2566 (res. ceph C) | 22 |
| Proteus vulgaris MB No. 2112 (episome) | 30 |
| Proteus mirabilis MB No. 3126 | 29 |
| Vibrio Percolans ATCC 8461 + 2×10$^5$ u/ml penicillinase | 25 |
| Vibrio percolans ATCC 8461 + β-lactamase | 34 |

TABLE IV-continued

| Organism | Inhib. Zone Diam., mm |
|---|---|
| from *Enterobacter clacae* MB 2646 | |

Antibiotic 890A$_{10}$ is active against various gram-positive and gram-negative bacteria and is a potent inhibitor of bacterial β-lactamases, and may find utility in human and veterinary medicine. 890A$_{10}$ may be used alone or in combination with other antibacterial drugs for treating infections caused by gram-positive or gram-negative bacteria, for example, against *Staphylococcus aureus*, *Proteus mirabilis*, *Escherichia coli*, *Klebsiella pneumoniae* and *Salmonella schottmuelleri*.

The compound of this invention may also be used in conjunction with β-lactam antibiotics susceptable to β-lactamases, to potentiate the action of such β-lactam antibiotics by inhibiting the lactamase activity and thus prolonging the life time of the antibiotics.

Thus, a combination of antibiotic 890A$_{10}$, with a lactamase-sensitive β-lactam antibiotic will be more efficacious for the treatment of infection with β-lactamase-producing bacteria than would the same quantity of β-lactamase-sensitive antibiotic alone.

Antibiotic 890A$_{10}$ may be utilized as an additive to animal feedingstuffs, for preserving foodstuffs and as disinfectants. It may be employed in aqueous compositions ranging from about 0.1 to about 100 parts of antibiotic per million parts of solution or preferably in concentrations ranging from about 1 to about 10 parts of antibiotic per million parts of solution in order to destroy and inhibit the growth of harmful bacteria on medical and dental equipment and as bactericides in industrial applications.

Antibiotic 890A$_{10}$ may be used in pharmaceutical preparations as the sole active ingredient or in combination with one or more other antibiotics or with one or more pharmacologically active substances.

The antibiotic may be administered orally, topically, intravenously or intramuscularly. The methods employed for administration may be any that are well known in the art or any to which the antibiotic herein described may be adapted.

Also, in addition to a carrier, the instant compositions may include other ingredients such as stabilizers, binders, antioxidants, preservatives, lubricators, suspending agents, viscosity agents or flavoring agents that are well known and commonly employed.

In veterinary medicine, such as in the treatment of chickens, cows, sheep, pigs and the like, the composition may, for example, be formulated as an intramammary preparation in either long acting or quick-release bases.

The dosage to be administered depends to a large extent upon the condition of the subject being treated, the weight of the host and the type of infection, the route and frequency of administration, the parenteral route being preferred for generalized infections and the oral route for intestinal infections.

In the treatment of bacterial infections in man, the compound of this invention may be co-administered with a β-lactamase-sensitive antibiotic orally or parenterally, in accordance with conventional procedures for antibiotic administration, the antibiotic 890A$_{10}$ being given, in an amount of from about 2 to 600 mg./kg./day and preferably about 5 to 100 mg./kg./day in preferably divided dosage, e.g. three to four times a day. It may be administered in dosage units containing, for example, 100, 330, 400 or 1000 mg. of active ingredient with suitable physiologically acceptable carriers or excipients. The dosage units are in the form of liquid preparations such as solutions or suspensions or as solids in tablets or capsules. It will, of course, be understood that the optimum dose in any given instance will depend upon the type and severity of infection to be treated, and that smaller doses will be employed for pediatric use, all of such adjustments being within the skill of the practitioner in the field.

Included in this invention are the non-toxic, pharmaceuticaly acceptable salts of 890A$_{10}$. For example, the pharmacologically acceptable salts formed with inorganic and organic bases; which include, for example, metal salts derived from alkali metal or alkaline earth metal hydroxides, carbonates, or bicarbonates, such as those derived from sodium, potassium, ammonium and calcium and salts derived from primary, secondary or tertiary amines such as monoalkylamines, dialkylamines, trialkylamines, lower alkanolamines, di-loeralkanolamines, lower alkylenediamines, N,N-diaralkyl lower alkylenediamines, aralkylamines, amino substituted lower alkanols, N,N-di-lower alkylamino substituted lower alkanols, aminopolyamino and guanidino-substituted lower alkanoic acids and nitrogen-containing heterocyclic amines. Representative examples include salts derived from sodium hydroxide, ammonium hydroxide, sodium carbonate, sodium bicarbonate, potassium carbonate, potassium hydroxide, calcium carbonate, trimethylamine, triethylamine, piperidine, N-ethylpiperidine, morpholine, quinine, lysine, protamine, arginine, procaine, ethanolamine, morphine, benzylamine, ethylenediamine, N,N'-dibenzylethylenediamine, diethanlamine, piperazine, dimethylaminoethanol, 2-amino-2-methyl-1-propanol, theophylline, N-methylglucamine and the like.

The salts of the compounds of the present invention may be isolated directly from fermentation media by the use of appropriate eluents during the ion exchange chromatography or prepared by conventional methods well known in the art. For example, the di-salts such as disodium salt may be obtained by treating two equivalents of sodium hydroxide with one mole of the product (I) in a suitable solvent. Also mixed salts with monovalent cations may be prepared by combining one mole of a monovalent base with one mole of the product (I) plus one equivalent of another base. Alternatively, monobasic salts may be obtained by treating one equivalent of a base having a monovalent cation, with one mole of the product (I). Also, salts may be formed by treating one mole of the product with one mole of a base having a divalent cation. The salts of this invention are pharmacologically acceptable non-toxic derivatives which can be used as the active ingredient in suitable unit-dosage pharmaceutical forms. Also, they may be combined with other drugs to provide compositions having a broad spectrum of activity.

Fermentation broths containing the antibiotic 890A$_{10}$ produced in accordance with the procedures described herein have activities ranging from about 2 to 170 units per ml. when assayed in accordance with the disc-diffusion assay using *Vibrio percolans* (ATCC 8461). The antibiotic 890A$_{10}$ contained in these fermentation broths can be recovered and purified by a number of procedures. One such procedure comprises adsorbing the antibiotic 890A$_{10}$ on a strongly basic anion exchange resin. Illustrative of such strongly basic anion exchange resins are those having a styrene-divinylbenzene matrix, for example the polystyrene nuclear quaternary ammonium resin Dowex 1×2 (manufactured by Dow Chemical Co., Midland, Michigan), on the chloride cycle. Other representative members of this class of strongly basic exchange resins include the following: Duolite A-40, A-42, A-101, A-102 and A-114 (manufactured by Chemical Process Co., Redwood City, California). Amberlite IRA-400, IRA-401 and IRA-410. Alternately, a weakly basic anion exchange resin such as Amberlite IRA-68 may be used. (Amberlite resins are manufactured by Rohm and Haas, Washington Square, Philadelphia, 5, Pennsylvania).

The adsorbed antibiotic is readily eluted from the anion exchange resin with salt solutions in 80% (v/v) aqueous methanol. The eluate so obtained can be further purified by other purification procedures. Thus, the eluate can be purified by concentrating it and passing it through a column packed with a polystyrene, nonpolar, hydrophobic crosslinked divinyl benzene polymer such as XAD-1, 2 and 4, or polyacrylamide resins such as XAD-7 and 8. XAD-2 is preferred. (XAD-1, 2, 4, 7, and 8 are manufactured by Rohm and Haas, Washington Square, Philadelphia 5, Penn.).

A method of obtaining further purified antibiotic 890A/$_{10}$ is by the use of gel filtration through polyacrylamide gel having a pore size which excludes molecules having a molecular weight greater than 1800, such as Bio-Gel P-2 (manufactured by Bio-Rad, Richmond, Calif.). Other gels, such as Sephadex G-10 may also be employed for desalting.

The preferred procedure by which antibiotic 890A$_{10}$ may be obtained in high purity from a broth consists of centrifugation or filtration of the broth to remove solids; an adsorption and elution of the filtrate from an anion-exchange resin such as Dowex-1×2 in the chloride cycle with 3% NaCl in 80% (v/v) aqueous methanol, which both concentrates and partially purifies the antibiotic; a passage over a column of suitably prepared XAD-2, which retards the antibiotic and thereby purifies and desalts the Dowex-1×2 eluate. The fractions enriched in 890A$_{10}$ are pooled and further purified. Chromatography on a Dowex-1×2 minus 400 mesh resin, with elution by NaCl and/or NH$_4$Cl in 80% aqueous methanol, gives a product freed from many of the original UV-absorbing impurities (the NH$_4$Cl is used to provide some buffering capacity in the eluent) and separates the 890A$_{10}$ from other antibiotics; a desalting on Bio-Gel P-2 or Sephadex G-10, removes most of the salt introduced in the Dowex-1×2 chromatography.

The remaining impurities may be reduced by an additional cycle of chromatography on Dowex-1×2, minus 400 mesh, with elution by a solution containing sodium chloride and 30% methanol followed by desalting.

In purification by column chromatography, in general only those fractions of the eluted volume which contain antibiotic at least 30% as pure as the purest fraction are combined for further purification. Criteria of purity are the ratios bioactivity/$A_{220}$, $A_{300}/A_{250}$ and HAEA$_{300}/A_{220}$; and, in desalting procedures, the conductivity. Thus at each chromatography step the $A_{220}$, $A_{250}$, $A_{300}$ and bioactivity of appropriate fractions are measured. Where possible, HAEA$_{300}$ is also measured, and in desalting, conductivities are measured. The criteria for deciding which fractions to combine for subsequent operations may be adjusted somewhat to achieve a higher yield, at the expense of purity, or conversely a higher purity at the expense of yield.

In laboratory-scale operations (less than 20 liters of sample volume), all chromatography steps except the XAD-2 chromatography are carried out in a cold room at 2°–5° C. The XAD-2 chromatography is carried out at room temperature. The pH of antibiotic solutions to be stored is adjusted to 7–8 by careful addition of dilute NaOH or HCl solutions. Aqueous solutions are stored in a refrigerator, or preferably in ice water, and 50%–80% methanol solutions are stored at −20° to −60° C.

At stages of purification prior to XAD-2 chromatography, solutions are generally brought to 25 μM in EDTA by addition of 1/4000th volume of a solution of 0.1M Na$_2$ EDTA which has been neutralized to pH 7.0 by addition of sodium hydroxide (0.1M "neutral EDTA").

A flow sheet diagram of the purification procedure for obtaining antibiotic 890A$_{10}$ is presented in FIG. 1.

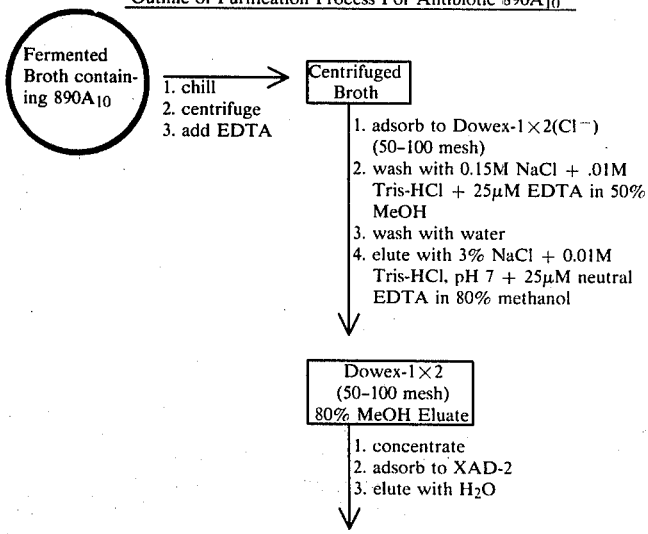

FIG. 1
Outline of Purification Process For Antibiotic 890A$_{10}$

FIG. 1
Outline of Purification Process For Antibiotic 890A$_{10}$

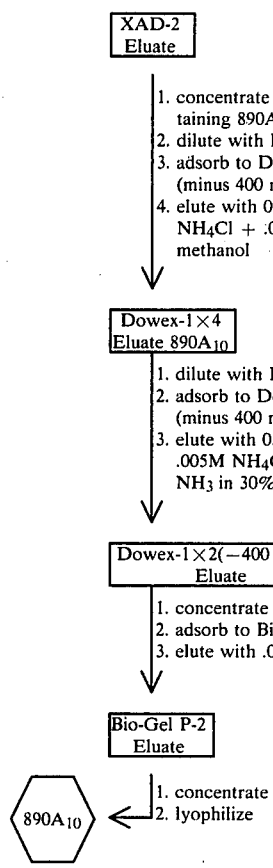

ASSAY PROCEDURES FOR ANTIBIOTIC 890A$_{10}$

I. Bioassay

An agar plate disc-diffusion method is employed using *Vibrio percolans* ATCC 8461 as tester organism. A purified sample of antibiotic 890A$_1$ is used as standard. Antibiotic 890A$_1$ is prepared according to the procedure set forth in Example 6.

Plates containing *Vibrio percolans* ATCC 8461 are prepared as follows:

A lyophilized culture of *Vibrio percolans* ATCC 8461 is suspended in 15 ml. of a sterilized medium containing 8 g./liter of Difco Nutrient Broth and 2 g./liter of yeast extract in distilled water "nutrient broth-yeast extract" (herein after designated NBYE). The culture is incubated overnight on a rotary shaker at 28° C. This culture is used to inoculate the surface of slants containing 1.5% agar in NBYE, and the inoculated slants are incubated overnight at 28° C., and then stored in a refrigerator.

The refrigerated slants prepared from a single lyophilized culture are used for up to four weeks from their preparation, as follows: A loop of inoculum from the slant is dispersed in 50 ml. of NBYE contained in a 250 ml. Erlenmeyer flask. The culture is incubated overnight on a rotary shaker at 28° C. and then diluted to a density giving 50% transmittance at 660 nm. A 33.2 ml. portion of this diluted culture is added to 1 liter of NBYE containing 15 g. of agar and maintained at 46° C. The inoculated agar-containing medium is poured into 100×15 mm. plastic petri dishes, 5 ml. per dish, chilled, and maintained at 2°–4° C. for up to 5 days before using.

Filter paper discs of one-half inch diameter are dipped into the solution to be assayed, and are placed on the agar. Alternatively, the discs may be loaded by pipetting one-tenth ml. of solution onto a dry disc, and then placing the disc on the agar. The diameter of the zone of inhibition is measured after appropriate incubation (12–14 hours at 25° C.). If necessary, dilutions of the solutions to be assayed are made in 0.05M potassium phosphate buffer, pH 7.4 "potassium phosphate buffer" (hereinafter referred to as KPB), or in deionized water.

Calculations of potencies proceed as follows: a slope is determined by measuring the zone diameters of a solution of antibiotic 890A$_{10}$ and of a fourfold dilution (in KPB) of this solution. Two discs of each concentration are assayed on a single plate, and the average zone size at each concentration is determined. The slope is equal to one-half of the difference of the average zone sizes. Potencies are then calculated by the formula:

$$\text{Potency (units/ml.)} = \left( \frac{[D - D_s] \log 2}{\text{slope}} \right)$$

$$(\text{Potency of Standard}) \times \text{Dilution} \times 10$$

where D is the average diameter of the zones formed by the unknown, D$_s$ is the average diameter of the standard zones, and "Dilution" is the degree to which the unknown was diluted before assay. If no standard is used, D$_s$ is assumed to be 25 mm. and (Potency of Standard) is taken as 1 unit/ml., when measured on *Vibrio percolans* ATCC 8461. Pure 890A$_1$ is defined as having a potency of 250 units per hydroxylamine-extinguishable absorbance unit at 300 nm, when used as a standard.

II. Assay Procedure for Determining "890 Assay Units"

A conventional agar plate disc-diffusion method is employed using *Vibrio percolans* ATCC 8461 as tester organism. Cephaloridine is employed as a standard. Plates containing *Vibrio percolans* ATCC 8461 are prepared as follows. A culture of *Vibrio percolans* ATCC 8461 is incubated in nutrient broth-yeast extract overnight on a rotary shaker at 28° C. and then diluted to a density of 60% transmittance at 660 nm. A 33.2 ml. portion of this diluted culture is added to 1 liter of a medium composed of nutrient agar plus 0.2% yeast extract maintained at 46° C. The inoculated agar-containing medium is poured into 100×15 mn. plastic-petri dishes, 10 ml. per dish, chilled, and maintained at 2°–4° C. for up to 5 days before use.

The concentration of cephaloridine which is equivalent to 1 unit/ml. of 890A$_1$ is determined by assay on plates prepared as above, but containing 5 ml. of inoculated medium per plate, as follows. Four concentrations of cephaloridine constitute the standard—3.12, 6.25, 12.5 and 25 mcg per ml. with the 12.5 mcg per ml. as a reference solution. The zone diameters on a 5 ml. plate for the standard are as follows:

| Conc. (mcg/ml.) | Zone Diameter (mm.) |
| --- | --- |
| 3.12 | 16.8 |
| 6.25 | 22.3 |
| 12.5 | 25.0 |
| 25 | 29.6 |

A unit is defined as the amount of antibiotic per ml. producing a 25 mm. zone of inhibition on a 5 ml. plate as described in section I above. Therefore, in this assay a concentration of 12.5 mcg per ml. of cephaloridine is considered equivalent to 1 unit of 890A$_1$ per ml. Since the slope of the line for cephaloridine is 4.0 calculations of the potency of a sample are made using a slope of 4.0

III. Hydroxylamine Reaction

Antibiotic 890A$_{10}$ reacts with hydroxylamine and produces a substance with greatly diminished absorbance at 300 nm. This provides the basis for a quantitative assay of the antibiotic 890A$_{10}$.

The solution to be assayed is brought to 0.05 M in potassium phosphate, pH 7.4 by adding 1/20th volume of a solution containing 0.8 M K$_2$HPO$_4$ and 0.2 M KH$_2$PO$_4$. Then one-hundredth volume of 1 M hydroxylamine hydrochloride is added, and the absorbance at 300 nm is measured at intervals of one-half to two minutes. The reaction is conducted at room temperature. First-order kinetics are assumed and a half-life is estimated from the absorbance decrease during the first ten minutes. From this half-life, the time is estimated beyond which no further absorbance decrease should be observed and observations are continued beyond that time. If no further decrease is observed beyond that time, the total absorbance decrease (correcting for dilution effect and absorbance of the hydroxylamine) is taken as the "Hydroxylamine-extinguishable absorbance at 300 nm (HAEA$_{300}$)". If absorbance decrease is observed beyond that time, the rate of background absorbance decrease is calculated, and the observed decrease at that time is corrected for background decrease, assuming that background decrease is linear with time. The corrected value is then recorded as the HAEA$_{300}$.

The number of HAEA$_{300}$ units is equal to the HAEA$_{300}$ multiplied by the volume in ml.

The examples which follow illustrate the methods by which the products of this invention may be obtained. However, the examples are illustrative only and it should be apparent to one having ordinary skill in the art that this invention includes the functionally equivalent products and methods for their preparation. Therefore, any modification of the processes described herein which results in the formation of the products of his invention should be construed as constituting an analogous method. The described processes are capable of wide variation and modification and any minor departure or extension is considered as being within the skill of the artisan and as falling within the scope of this invention.

The preparation of antibiotic 890A$_1$ as described in the pending patent application of Cassidy et al., U.S. Ser. No. 634,300, filed Nov. 21, 1975 is hereby incorporated by reference.

EXAMPLE 1

A slant culture containing MA-4638 is used to inoculate a 250-ml. baffled Erlenmeyer flask containing 50 ml. of Medium A.

| Medium A | |
| --- | --- |
| Dextrose | 10.0 g. |
| Yeast Autolysate (Ardamine*) | 10.0 g. |
| MgSO$_4$ . 7H$_2$O | 0.05 g. |
| Phosphate Buffer** | 2.0 ml. |
| Distilled Water | 1000 ml. |
| pH 6.5 | |
| *Ardamine: Yeast Products, Inc. | |
| **Phosphate buffer solution: | |
| KH$_2$PO$_4$ | 91.0 g. |
| Na$_2$HPO$_4$ | 95.0 g. |
| Distilled Water | 1000 ml. |

This flask is shaken at 28° C. on a 220 rpm shaker, 2-inch throw for two days when growth is satisfactory. After two days, this seed is used to inoculate three 250-ml. Erlenmeyer flasks containing 40 ml. Medium B using 2 ml. per flask (5%).

| Medium B | |
| --- | --- |
| Tomato Paste | 20.0 g. |
| Whole Oats (ground) | 20.0 g. |
| Distilled Water | 1000 ml. |
| pH: adjust to 7.0 using NaOH | |

These production flasks are also shaken at 28° C. on a 220 rpm shaker for up to four days with assays run during the fermentation. At three days age, an aliquot of the supernatent from centrifuged broth is submitted for classification and identification studies. Using 1/4 inch assay discs on standard assay plates, this broth gives a 22 mm. zone of inhibition against *Proteus vulgaris* and a 15 mm. zone against *Salmonella gallinarum*. Bioautography of an electrophoretogram of the centrifuged broth shows two components. The faster moving smaller spot contains 890A$_{10}$.

EXAMPLE 2

Two frozen vials each containing 2 ml. of MA-4638 inoculum are slowly thawed, and the contents aseptically transferred to two seed flasks each containing 500 ml. of C Medium. The seed flask, 2-liter, triple-baffled shake flask equipped with a side arm, is stoppered with cotton.

| C Medium | |
|---|---|
| Autolyzed Yeast (Ardamine*) | 10.0 g. |
| Glucose | 10.0 g. |
| $MgSO_4 \cdot 7H_2O$ | 0.05 g. |
| Phosphate Buffer** | 2.0 ml. |
| Distilled water | 1000 ml. |
| pH adjusted to 6.5 with NaOH before sterilization | |
| * Ardamine: Yeast Products, Inc. | |
| **Phosphate buffer solution: | |
| $KH_2PO_4$ | 91.0 g. |
| $Na_2HPO_4$ | 95.0 g. |
| Distilled Water | 1000 ml. |

The inoculated seed flasks are shaken for 24–30 hours at 28° C.±1° C. on a 210 rpm gyrotory shaker, 2-inch throw.

The growth from the seed flasks are used to inoculate two 14-liter glass fermentors containing 10 liters of production medium (D medium plus 0.15% soybean oil, v/v).

| D Medium | |
|---|---|
| Dextrin (CPC Modified Starch) | 40.0 g. |
| Distiller's Solubles | 7.0 g. |
| Yeast Extract | 5.0 g. |
| $CoCl_2 \cdot 6H_2O$ | 50.0 mg. |
| Distilled Water | 1000 ml. |
| pH adjusted to 7.3 with NaOH before sterilization | |

The fermentors are operated at 24° C. using an agitation rate of 640 rpm (about Kd 5.5), and an air flow of 0.5 VVM, for 72 hours. Defoamer, Hodag-MF (Hodag Chemical Corp.) is used as required, but not to exceed 0.1%.

Contents of the two fermentors are pooled after the fermentation run, about 20 liters.

200-Ml. portions of the batch are centrifuged in a Servall RC-2B centrifuge at 9000 rpm for 20 minutes. The supernatant is filtered through a 1 cm. bed of Hyflo Super-Cel in a 13-inch Lapp funnel with a cloth filter. The filtrate has a bioactivity of 20 units/ml.

The filtered broth, (18 liters) is applied to a column (8.2×29 cm.) of Dowex-1×2($Cl^-$) 50–100 mesh, at 150 ml./min. The column is then washed with 1 liter of de-ionized water followed by 15 liters of 0.15M NaCl+0.01M Tris-HCl buffer, pH 7.0+25 μM neutral EDTA in 50% MeOH at 150 ml./min.

The antibiotic $890A_{10}$ is then eluted with 3.2% NaCl+0.02M Tris-HCl buffer pH 7.0+25 μM neutral EDTA in 80% MeOH at 100 ml./min. Fractions are collected as follows: one fraction of 1 liter, four fractions of 500 ml. each, and twelve fractions of 1 liter each are collected. Bioactivity and absorbance at 220 nm is measured on each fraction, and those fractions leaving bioactivity/$A_{220}$ ratios of greater than 0.6 units/$A_{220}$ unit, and which also contained more than 10% of the total recovered activity per fraction are combined for further purification. Thus, fractions 4 through 8 are combined, containing a total of 22% of the applied bioactivity.

The pooled fractions are concentrated under reduced pressure to 190 ml., the precipitated salt is washed with deionized water, and the wash is added to the supernatant, bringing the final volume to 220 ml. The concentrate is adjusted to pH 6.5 with HCl and is applied on a column (6.0×59 cm.) of Amberlite XAD-2 which has been previously washed with 8 liters of 60% aqueous acetone followed by 16 liters of deionized water. After application is completed, the column is rinsed with 5×10 ml. portions of deionized water, and the antibiotics are eluted with deionized water at 35 ml./min. Fractions are collected as follows: one fraction of 500 ml. followed by seven fractions of 250 ml. each, followed by four fractions of 500 ml.

Bioactivity and $HAEA_{304}$ values are measured on fractions from 3 through 12. Fractions 4 through 9 have $HAEA_{304}/A_{220}$ ratios greater than 0.01, and are combined for further purification. Fraction 3, containing about one-fifth of the applied salt, is also added to this pool. The combined pool contains 469 $HAEA_{304}$ units.

The pooled fractions are diluted to 4.1 liters and are applied to a column (2.15×42 cm.) of Dowex-1×4($Cl^-$) minus 400 mesh at 2 ml./min. The column is washed with 100 ml. of 50% methanol, and the antibiotic is eluted with 0.25 M NaCl+0.01 M $NH_4Cl$+0.0001 M $NH_3$ in 80% MeOH at approximately 2 ml./min. Fractions of from 8 to 12 ml. are collected.

The bioactivity and the absorbance at 220 nm, 260 nm, and 300 nm are measured for every fifth fraction, and $HAEA_{300}$ is measured on the peak bioactive fractions. The $890A_{10}$ bioactivity appears in fractions 85 through 150, with a maximum at fraction 120. Fractions with $HAEA_{300}/A_{300}$ values greater than 0.05 are combined for further purification. Thus, fractions 105 through 133 are combined, containing a total of 130 $HAEA_{300}$ units. The pooled fractions 105 through 133 are diluted to 1900 ml. with deionized water, and the pH is adjusted to 7.6. The sample is applied to a column (2.15×42 cm.) of Dowex-1×2($Cl^-$), minus 400 mesh, which has been previously washed with 3 liters of 3% NaCl in 50% methanol followed by 50 ml. of 50% methanol. After the entire sample has been applied, the column is washed with 100 ml. of 30% methanol, and is eluted at 2 ml./min. with 0.26 M NaCl+0.005 M $NH_4Cl$+0.0002 M $NH_3$ in 30% methanol. Fractions of 10 to 12 ml. are collected.

The main peak of antibiotic $890A_{10}$ appears in fractions 230 to 290, with a maximum at fraction 260. Those fractions with an $A_{300}/A_{250}$ ratio greater than 1.10 and an $A_{300}/A_{220}$ ratio greater than 0.83 are combined for further purification. Thus, fractions 240 through 275 are combined, containing 91.6 $HAEA_{300}$ units.

The combined fractions 240 through 275 are concentrated under reduced pressure to 10 ml., and the concentrate is separated from the precipitated salt by pipetting. The salt is washed with 2 ml. deionized water, and the wash is added to the concentrate. The combined 12 ml. of concentrate and wash is applied to a column (2.15×76 cm.) of Bio-Gel P-2 (200–400 mesh), which has been previously washed with 30 ml. of saturated NaCl in deionized water, followed by 1500ml. of deionized water and 50 ml. of 0.05 mM$NH_3$ in deionized water. After application is complete, the column is rinsed with 3×1 ml. rinses of 0.05 mM$NH_3$ in deionized water, and the antibiotic is eluted with 0.05 mM$NH_3$ in deionized water at 0.73 ml./min. Fractions of 3.65 ml. each are collected.

The main peak of antibiotic 890A$_{10}$ appears in fractions 29 through 50, with a maximum at fraction 36. Those fractions having an A$_{300}$/A$_{250}$ ratio greater than 1.9, and also having an A$_{300}$/A$_{220}$ ratio greater than 1.45, are combined for lyophilization and NMR analysis. Thus, fractions 36 through 45 are combined, containing 50.8 A$_{300}$ units, of which 45.1 is hydroxylamine-extinguishable.

The combined fractions 36 through 45 are concentrated under reduced pressure to 1 ml., and 5 ml. D$_2$O are added. The sample is again concentrated to 0.835 ml., and 0.825 ml. of this is transferred to a glass vial and freeze-dried and lyophilized. The lyophilized sample contains 48.2 A$_{300}$ units and has 4.6 mg. of solids. This is designated sample 9441-154.

The side fractions 31-34 and 46-49 are combined to give a "side pool" which is then concentrated to 1 ml., quick-frozen, and lyophilized. These fractions contain 24 A$_{300}$ units of which 17 are hydroxylamine-extinguishable. This sample is designated 9441-155.

EXAMPLE 3

A frozen vial containing 2 ml. of MA-4638 inoculum is slowly thawed, and the content aseptically transferred to a seed flask containing 500 ml. of C Medium. The seed flask, 2-liter, triple-baffled shake flask equipped with a side arm, is stoppered with cotton.

| C Medium | |
|---|---|
| Autolyzed Yeast (Ardamine*) | 10.0 g. |
| Glucose | 10.0 g. |
| MgSO$_4$ . 7H$_2$O | 0.05 g. |
| Phosphate Buffer** | 2.0 ml. |
| Distilled water | 1000 ml. |
| pH adjusted to 6.5 with | |
| NaOH before sterilization | |
| * Ardamine: Yeast Products, Inc. | |
| **Phosphate buffer solution: | |
| KH$_2$PO$_4$ 91.0 g. | |
| Na$_2$HPO$_4$ 95.0 g. | |
| Distilled Water 1000 ml. | |

The inoculated seed flask is shaken for 36 hours at 28° C. ±1° C. on a 210 rpm gyrotory shaker, 2-inch throw.

The growth from this seed flask is used to inoculate a 14-liter glass fermentor containing 10 liters of production medium (D medium plus 0.15% soybean oil, v/v).

| D Medium | |
|---|---|
| Dextrin (CPC Modified Starch) | 40.0 g. |
| Distiller's Solubles | 7.0 g. |
| Yeast Extract | 5.0 g. |
| CoCl$_2$ . 6H$_2$O | 50.0 mg. |
| Distilled Water | 1000 ml. |
| pH adjusted to 7.3 with | |
| NaOH before sterilization | |

The fermentor is operated at 24° C. using an agitation rate of 550 rpm (Kd 3.0-3.5), and an air-flow of 0.5 VVM. Defoamer, Hodag-MF (Hodag Chemical Corp.) is used as required, but not to exceed 0.1%.

The culture broth is harvested after 72 hours of fermentation.

200-Ml. portions of the batch are centrifuged in a Servall RC-2 centrifuge at 9000 rpm. The supernatant contains seven liters with 39 bioassay units per ml.

The supernatant is filtered through a Lapp funnel containing a 1-cm. layer of Hyflo Super-Cel on a cloth filter. To the 6.5 liters of filtrate are added 3.25 ml. of 0.1 M neutral EDTA, and the filtrate is then applied to a column (8.2×21.5 cm.) of Dowex-1×2(Cl$^-$), 50–100 mesh, at 60 ml./min. After application, the column is rinsed with 1 liter of deionized water, and is then washed with 12 liters of 0.15 M NaCl+0.02 M Tris-HCl buffer, pH 7.08+25 μM EDTA in 50% MeOH at 50 ml./min.

The antibiotic 890A$_{10}$ is then eluted with 12.3 liters of 3% NaCl+0.02 M Tris-HCl buffer, ph 7.1+25 μM EDTA in 80% MeOH at 60 ml./min.

Fractions are collected as follows: one fraction of 500 ml., four fractions of 200 ml. each, twelve fractions of 500 ml. each, and five fractions of 1 liter each. Bioactivity appears in fractions 3 through 17, with a maximum at fractions 6, 7 and 8. Those fractions with bioactivity/A$_{220}$ values greater than 0.9 units/A$_{220}$ unit, which also contains more than 8% of the total recovered activity per fraction are pooled for further purification. Thus, fractions 6 through 12 are combined, containing 106,000 bioassay units, or 41% of the applied bioactivity. These pooled fractions are held at −60° C. until they are combined with fractions 6 through 13 from a second Dowex column, as described in Example 4.

EXAMPLE 4

Two frozen vials each containing 2 ml. of MA-4638 inoculum are slowly thawed, and the contents aseptically transferred to two seed flasks each containing 500 ml. of C medium. The seed flask, 2-liter, triple-baffled shake flask equipped with a side arm, is stoppered with cotton.

| C Medium | |
|---|---|
| Autolyzed Yeast (Ardamine*) | 10.0 g. |
| Glucose | 10.0 g. |
| MgSO$_4$ . 7H$_2$O | 0.05 g. |
| Phosphate Buffer** | 2.0 ml. |
| Distilled water | 1000 ml. |
| pH adjusted to 6.5 with | |
| NaOH before sterilization | |
| * Ardamine: Yeast Products, Inc. | |
| **Phosphate buffer solution: | |
| KH$_2$PO$_4$ 91.0 g. | |
| Na$_2$HPO$_4$ 95.0 g. | |
| Distilled Water 1000 ml. | |

The inoculated seed flasks are shaken for 36 hours at 28° C. ±1° C. on a 210 rpm gyrotory shaker, 2-inch throw.

The growth from the seed flasks are used to inoculate two 14-liter glass fermentors each containing 10 liters of D production medium.

| D Medium | |
|---|---|
| Dextrin (CPC Modified Starch) | 40.0 g. |
| Distiller's Solubles | 7.0 g. |
| Yeast Extract | 5.0 g. |
| CoCl$_2$ . 6H$_2$O | 50.0 mg. |
| Distilled Water | 1000 ml. |
| pH adjusted to 7.3 with | |
| NaOH before sterilization | |

Two fermentors are charged and operated at 24° C. using an agitation rate of 550 rpm (Kd 3.0-3.5) and an air flow of 0.5 VVM. Defoamer, Polyglycol 2000, is used as required, but not to exceed 0.1%.

The culture broths from the two fermentors are harvested after 72 hours.

200-Ml. portions of the 10-liter batches are centrifuged in a Servall at 9000 rpm yielding 9 liters of supernatant from each batch. Bioassays show that batch I has 23.4 units/ml. and batch II has 31.8 units/ml.

The batches are combined and chilled and filtered through a 1-cm. bed of Hyflo Super-cel on a 13-inch LabTek porcelain Buchner funnel. To the 15 liters of filtrate, 7.5 ml. of 0.1 M neutral EDTA is added.

The filtrate is applied on a column (13.4×16 cm.) of Dowex-1×2($Cl^-$), 50–100 mesh, at 100 ml. per minute. After application is complete, the column is washed with 2 liters of deionized water, and then with 20 liters of 0.15 M NaCl+0.01 M Tris-HCl buffer ph 7.01+25 $\mu$M EDTA in 50% MeOP, at 40–80 ml./min.

The antibiotic 890A$_{10}$ is then eluted with 24.4 liters of a solution containing 3% NaCl+0.02 M Tris-HCl, pH 7.0+25 $\mu$M EDTA in 80% MeOH, at 100 ml./min. Fractions are collected as follows: one 800 ml. fraction, four 400 ml. fractions, twelve 1000 ml. fractions, and five 2000 ml. fractions.

Antibiotic activity appears in fractions 5 through 16, with a maximum at fractions 7 and 8. The total activity in these fractions is 212,000 units, equal to 51% of the applied activity. Fractions 6 through 13 are combined for further purification.

The combined fractions 6 through 13 from the Dowex column are added to the combined fractions 6 through 12 from the Dowex column of Example 3, and are concentrated to 2.6 liters under reduced pressure in a steam-jacketed, long-tube evaporator. This concentrate is further reduced to 300 ml. by evaporating under reduced pressure in a rotary evaporator, and filtering off the precipitated salt crystals.

The concentrate is adjusted to pH 6.48 by addition of 1.7 ml. of concentrated hydrochloric acid, and is then applied to a column (8.1×59 cm.) of Amberlite XAD-2, and the column is rinsed with 3×20 ml. rinses of deionized water. The antibiotic is eluted with deionized water at a flow rate of 60 ml./min. Fractions are collected as follows: one fraction of 1 liter, seven fractions of 500 ml. each, and eight fractions of 1000 ml. each are collected and chilled in ice immediately after collection.

Both bioassay and HAEA$_{300}$ values are determined for each fraction, as well as the A$_{220}$, A$_{260}$, and A$_{300}$ values. Those fractions with HAEA$_{300}$/A$_{300}$ values greater than 0.075 are combined for further processing. Thus fractions 5 through 9 are combined, containing 164,000 bioassay units.

The pooled fractions are concentrated under reduced pressure to 100 ml., and 200 ml. of methanol is added. The sample is then applied to a column (2.15×38 cm.) of Dowex-1×4($Cl^-$) minus 400 mesh, at 2 ml./min. After application, the column is washed with 100 ml. of 80% methanol, and the antibiotic is eluted with 0.26 M NaCl+0.005 M NH$_4$Cl+0.00005 M NH$_3$ in 80% MeOH, at 2 ml./min. Fractions of 10 ml. each are collected.

Bioactivities and the values for A$_{300}$, A$_{250}$, A$_{220}$ and HAEA$_{300}$ are measured on every fifth fraction. Those fractions with HAEA$_{300}$/A$_{220}$ ratios greater than 0.07 are combined for further purification. Thus fractions 125 through 150 are combined.

To the combined fractions 125 through 150, from the Dowex 1×4 column is added lyophilized sample 9441-155 from Example 2, redissolved in 1.0 ml. of deionized water. This combined sample is diluted to 1900 ml. with deionized water and is applied to a Dowex-1×2($Cl^-$) column (2.15×40 cm., minus 400 mesh), at 2 ml./min. The column is rinsed with 150 ml. of 30% methanol and the antibiotic is then eluted with six liters of 0.25 M NaCl+0.005 M NH$_4$Cl+0.00005 M NH$_3$ in 30% MeOH at 2 ml./min. Fractions of 11.1 ml. each are collected.

The absorbance at 300 nm, 250 nm, and 220 nm is measured for every fifth fraction. The main peak of antibiotic 890A$_{10}$ appears in fractions 360 through 430, with a maximum in fractions 394–400. All fractions with an A$_{300}$/A$_{220}$ ratio greater than 1.30 are combined for further purification. Thus, fractions 380 through 420 are combined. These combined fractions contain 202 A$_{300}$ units, of which 197 are hydroxylamine-extinguishable.

To the combined fractions 380 through 420 is added the Sample 9441-154 from Example 2, which has been dissolved in 1 ml. of D$_2$O plus 4 ml. of deionized H$_2$O, and which contains 30.5 HAEA$_{300}$ units. The combined sample is diluted to 2.0 liters with deionized water and is applied to a column (2.15×41 cm.) of Dowex-1×2($Cl^-$), 200–400 wash, at 0.6 to 2 ml./min. The column is rinsed with 360 ml. of 30% methanol, and the antibiotic 890A$_{10}$ is eluted with 0.25 M NaCl+0.005 M NH$_4$Cl+0.00005 M NH$_3$ in 30% MeOH at 1.9 ml./min. Fractions of 9.7 ml. are collected.

The absorbance at 300 nm, 250 nm, and 220 nm is measured for every fifth fraction. The main peak of antibiotic 890A$_{10}$, as judged by the absorbance at 300 nm, appears in fractions 270 through 358, with a maximum at fraction 315. The fractions with A$_{300}$/A$_{220}$ ratios greater than 1.75 are combined for further purification. Thus, fractions 295 through 335 are combined, containing 145 A$_{300}$ units, of which 137 are hydroxylamine-extinguishable.

The combined fractions 295 through 335 are concentrated under reduced pressure to 10 ml. and the concentrate is adjusted to pH 7.0 with 1 M NaOH. The concentrate is applied to a column (2.15×75 cm.) of Bio-Gel P-2, 200–400 mesh, and the column is rinsed with 3×1 ml. rinses of deionized water. The antibiotic is eluted with deionized water at 0.6 ml./min. Fractions of 6.4 ml. each are collected.

The absorbance values at 300 nm, 250 nm, and 220 nm as well as the conductivities are measured on every second fraction. The main peak of absorbance at 300 nm appears in fractions 9 through 27 with a maximum at fraction 14. Fractions 11 through 16 have conductivities proportional to the A$_{300}$ value, and these are combined for mass spectrometric and NMR analysis. This pool contains 75.4 A$_{300}$ units in 38.7 ml. Of this, 34.7 ml. is concentrated to 1.22 ml. A 1.20-ml. portion of this is frozen and lyophilized for NMR analysis, yielding 2.84 mg. of solids. The remaining 4 ml. are converted to the NH$_4^+$ form by passage over a column (0.7×15 cm.) of Dowex-50W×2(NH$_4^+$) 200–400 mesh. The resulting ammonium salt is concentrated to 0.11 ml., 10 $\mu$l is removed, 100 $\mu$l of deionized water is added and four samples of forty-ml. each are removed and individually frozen and lyophilized for mass spectrometric analysis [9441-209-2].

Biogel fractions 17 through 23, containing 29.4 A$_{300}$ units, are also concentrated to 1 ml., frozen and lyophilized, giving 1.80 mg. of solids.

EXAMPLE 5

Two frozen vials each containing 1 ml. of MA-4638 culture broth are slowly thawed, and the contents are aseptically transferred to two 250-ml. triple-baffled Erlenmeyer flasks, each containing 50 ml. of C seed medium. The flasks are stoppered with cotton.

| C Medium | |
| --- | --- |
| Autolyzed Yeast (Ardamine*) | 10.0 g. |
| Glucose | 10.0 g. |
| MgSO$_4$ . 7H$_2$O | 0.05 g. |
| Phosphate Buffer** | 2.0 ml. |
| Distilled Water | 1000 ml. |
| pH adjusted to 6.5 with | |
| NaOH before autoclaving | |
| *Ardamine: Yeast Products. Inc. | |
| **Phosphate buffer solution: | |
| KH$_2$PO$_4$ | 91.0 g. |
| Na$_2$HPO$_4$ | 95.0 g. |
| Distilled Water | 1000 ml. |

Two seed flasks are shaken for 20-24 hours at 28° C. ±1° C. on a 210 rpm gyrotory shaker, 2-inch throw. Then the contents are pooled and used to inoculate production flasks.

Ten 2-liter baffled shake-flasks, each containing 300 ml. of D production medium, are inoculated with 10 ml. per flask of the broth from the seed flask. The above production flasks are covered with gauze closures.

| D Medium | |
| --- | --- |
| Dextrin (CPC Modified Starch) | 40.0 g. |
| Distiller's Solubles | 7.0 g. |
| Yeast Extract | 5.0 g. |
| CoCl$_2$ . 6H$_2$O | 50.0 mg. |
| Distilled Water | 1000 ml. |
| pH adjusted to 7.3 with | |
| NaOH before autoclaving | |

After inoculation, the production flasks are incubated at 24° C. ±1° C. with shaking on a 210 rpm gyrotory shaker, 2-inch throw, for three days. The flasks are harvested, contents pooled and the broth is assayed for activity.

| Harvest Age (hours) | 72 |
| --- | --- |
| pH | 6.5 |
| 890 Assay (units/ml.) | 30.45 |

Two liters of whole broth from the above D production flasks are centrifuged in 200-ml. portions at 9000 rpm to give 1.7 liters of supernatant with pH 6.8.

The supernatant is applied to a Dowex-1×2(Cl$^-$) 50–100 mesh column, bed dimensions 3.9×25 cm., at a flow rate of 5–10 ml. per minute. The column is washed with 50 ml. of deionized water, followed by 2 liters of 0.15 M NaCl+0.02 M Tris-HCl buffer, pH 7.0, +25 μM neutral EDTA in 50% (v/v) aqueous methanol.

The product is then eluted with 30 g./liter NaCl+0.02 M Tris-HCl buffer, pH 7.0+25 μM EDTA in 80% (v/v) aqueous methanol, at a flow rate of 5 ml./minute. Fractions of 10 ml. are collected.

Bioactivity appears in fractions 5 through 180, with a maximum at fractions 25 through 70. Fractions 12 through 105 are combined and concentrated to 15 ml. under reduced pressure. The pH is adjusted to 6.5 with 1 M HCl, and the concentrate is applied to a column (3.4×55 cm.) of XAD-2 which has been washed with 2.5 liters each of 60% (v/v) aqueous acetone, deionized water, and 5% NaCl in deionized water. The column is rinsed with 3×5 ml. portions of deionized water and is eluted with deionized water at 10 ml./minute. Fractions of 10 ml. are collected.

Bioactivity appears in fractions 32 through 270 with a maximum at fractions 42 through 62. The total bioactivity eluting is 25% of the activity of the original broth. Fractions 40 through 240 are combined, and the stored combined fractions 12 through 34 from the XAD-2 column of Example 1 are added. The total combined fractions are concentrated under reduced pressure to 50 ml., containing 120 HAEA$_{304}$ units.

The concentrate is diluted with 200 ml. methanol, and applied at 2 ml./minute on a column (2.15×40 cm.) of Dowex-1×4, minus 400 mesh, which has been previously washed with 2 liters of 30 g./l. NaCl in 80% aqueous methanol, and 1 liter of 80% aqueous methanol. After application of the sample, the column is washed with 100 ml. of 80% (v/v) aqueous methanol and is eluted with 2.5 liters of 0.22 M NaCl+0.01 M NH$_4$Cl+0.0002 M NH$_3$ in 80% (v/v) aqueous methanol, followed by 3 liters of 0.31 M NaCl+0.01 M NH$_4$Cl+0.0002 M NH$_3$ in 80% (v/v) aqueous methanol. The flow rate is 2 ml./minute, and fractions of 10 ml. each are collected.

Antibiotic 890A$_{10}$ is separated on the Dowex-1×4 column eluted in fractions 155 through 195, as measured by assay on ATCC 8461.

EXAMPLE 6

Antibiotic 890A$_1$

A tube of lyophilized culture of *Streptomyces flavogriseus* MA-4600 NRRL 8140 is aseptically opened and the contents suspended in a tube containing 1.5 ml. of sterile Medium E having the following composition.

| Medium E | |
| --- | --- |
| Yeast Extract | 10.0 g. |
| Glucose | 10.0 g. |
| MgSO$_4$ . 7H$_2$O | 0.05 g. |
| Phosphate Buffer** | 2 ml. |
| Distilled H$_2$O | 1000 ml. |
| **Phosphate buffer solution: | |
| KH$_2$PO$_4$ | 91.0 g. |
| Na$_2$HPO$_4$ | 95.0 g. |
| Distilled H$_2$O | 1000 ml. |

This suspension is used to inoculate a 250-ml. triple-baffled Erlenmeyer seed flask containing 54 ml. of seed Medium C having the following composition.

| Medium C | |
| --- | --- |
| Autolyzed Yeast (Ardamine*) | 10.0 g. |
| Glucose | 10.0 g. |
| MgSO$_4$ . 7H$_2$O | 0.05 g. |
| Phosphate Buffer** | 2 ml. |
| Distilled H$_2$O | 1000 ml. |
| pH adjusted to 6.5 with NaOH | |
| *Ardamine: Yeast Products Corporation | |
| **Phosphate buffer solution: | |
| KH$_2$PO$_4$ | 91.0 g. |
| Na$_2$HPO$_4$ | 95.0 g. |
| Distilled H$_2$O | 1000 ml. |

The seed flask is stoppered with cotton and shaken for 30 hours at 28° C. ±1° C. on a 220 rpm gyrotory shaker, 2-inch throw.

Fifty 250 ml. unbaffled Erlenmeyer production flasks, each containing 40 ml. of production Medium F are inoculated with 1 ml. per flask of the broth from the seed flask. The production flasks are stoppered with cotton.

| Medium F | |
|---|---|
| Tomato Paste | 20.0 g. |
| Primary Yeast | 10.0 g. |
| Dextrin (Amidex) | 20.0 g. |
| CoCl$_2$ . 6H$_2$O | 5.0 mg. |
| Distilled H$_2$O | 1000 ml. |
| pH adjusted to 7.2–7.4 with NaOH | |

After inoculation, the production flasks are incubated at 28° C. ±1° C. with shaking on a 220 rpm gyrotory shaker, 2-inch throw for three days. The flasks are assayed for activity against standard *Vibrio percolans* ATCC 8461 assay plates using ½ inch assay discs dipped into centrifuged fermentation broth samples. Samples are diluted with 0.05 M phosphate buffer, pH 7.4. The results are tabulated below.

| Harvest Age Hours | 72 |
|---|---|
| pH | 6.4 |
| *Vibrio percolans* | |
| (1/100 Dilution) Assay | 23 mm. |
| 890 Assay, units/ml. | 103 |

The whole broth is centrifuged in 200 ml. portions in polycarbonate bottles at 9000 rpm for 15 minutes to give 1600 ml. of combined supernatants with a potency of 104 units/ml. To this is added 0.5 ml. of 0.1 M neutral EDTA.

The centrifuged broth is adsorbed on a Dowex-1×2 (Cl$^-$), 50–100 mesh column, bed dimensions 3.8×22 cm., at a flow rate of 6 to 20 ml./min. The column is rinsed with 100 ml. of deionized water and eluted with 1 liter of deionized water containing 50 g. of sodium chloride, 0.02 M Tris HCl buffer, pH 7.0, and 25 μM neutral EDTA, at a flow rate of 6 ml./min. Fractions of 10 ml. are collected.

Antibiotic 890A$_1$ appears in fractions 13 through 81, with a maximum at fractions 25 to 33, counting from the first application of salt eluate. Fractions 24 through 41, having the highest biopotency/A$_{220}$ ratios, are combined for further processing. The combined fractions have a total of 29,000 units, or 17% of the applied bioactivity.

The Dowex eluate is concentrated to 10 ml., the pH is adjusted to 6.5 with dilute hydrochloric acid, and the concentrate is applied on a column of XAD-2, bed dimensions 3.3×36 cm., which had been previously washed with 2 liters each of 60% aqueous acetone, deionized water, and 5% (w/v) sodium chloride in deionized water. The sample is eluted with deionized water at a flow rate of 6 ml./min. Fractions of 40 to 260 ml. are collected.

Antibiotic activity appears in fractions 6 through 14, extending from 220 to 2560 ml. of eluted volume. The peak is at fractions 9 and 10, extending from 370 to 590 ml. of eluted volume. Fractions 9 through 12, extending from 370 to 1060 ml. of eluted volume, have the highest ratios of HAEA$_{300}$/A$_{220}$, and are combined for further processing. These fractions have 36,600 units, equal to 126% of the apparent applied activity.

The combined fractions 9 through 12 are concentrated to 100 ml. and the concentrate applied on a column of Dowec-1×4 (Cl$^-$), minus 400 mesh, bed dimensions 2.2×41 cm., at a flow rate of 2 ml./min. The column is rinsed with 50 ml. of deionized water, and eluted with 3 liters of 0.07 M NaCl+0.005 M NH$_4$Cl+0.0001 M NH$_3$ in deionized water, at a rate of 2 ml./min. Fractions of 10.8 ml. are collected, starting from the first application of eluent.

The main peak of antibiotic 890A$_1$ appears in fractions 181 through 217, with a maximum at fraction 198. Fractions 186 through 210, containing a total of 114 absorption units at 300 nm., are pooled.

The pooled fractions are concentrated to 4.0 ml., and the pH is adjusted to 7.3 by addition of 16 μ liter of 1 M NaOH. The concentrate is applied on a column of Bio-Gel p-2, 200–400 mesh, bed dimension 2.15×70 cm., and is washed in with 3×1 ml. washes of deionized water and eluted with deionized water at 0.96 ml./min. Fractions of 3.85 ml. are collected.

The main peak of antibiotic 890A$_1$ appears in fractions 24 through 44, with a maximum at fractions 33 and 34. Fractions 27 through 38, having the highest A$_{300}$/A$_{245}$ ratios, are combined for lyophilization. These combined fractions have a total of 72 A$_{300}$ units.

To carry out the lyophilization, the combined fractions are concentrated to 3.0 ml. and the pH of the concentrate is adjusted to 7.5 by addition of 10 μ liters of 0.1 M NaOH. The sample is divided into two portions of 1.50 ml. each, and the portions are separately quick-frozen and lyophilized from 14 ml. glass screw-cap vials. Each sample contains 1.73 mg. of 890A$_1$, corresponding to 35.8 A$_{300}$ units.

What is claimed is:

1. A method for the production of the compound 890A$_{10}$ having the structure:

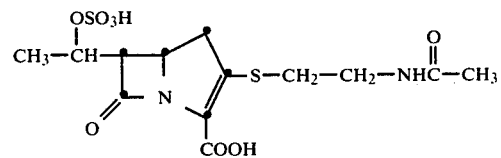

which comprises cultivating a 890A$_{10}$-producing strain of *Streptomyces flavogriseus* in an aqueous nutrient medium containing assimilable sources of carbon, nitrogen and inorganic salts under submerged aerobic conditions and recovering said antibiotic.

2. The process of claim 1 wherein the microorganism cultivated is *Streptomyces flavogriseus* NRRL 11,020.

* * * * *